United States Patent
Neftel

(10) Patent No.: US 9,125,989 B2
(45) Date of Patent: Sep. 8, 2015

(54) DEVICE FOR DETERMINING THE CHARACTERISTICS OF PERITONEAL MEMBRANE

(75) Inventor: Frédéric Neftel, Lausanne (CH)

(73) Assignee: DEBIOTECH S.A., Lausanne (CH)

(*) Notice: Subject to any disclaimer, the term of this patent is extended or adjusted under 35 U.S.C. 154(b) by 850 days.

(21) Appl. No.: 13/180,547

(22) Filed: Jul. 12, 2011

(65) Prior Publication Data

US 2012/0029325 A1    Feb. 2, 2012

Related U.S. Application Data

(63) Continuation-in-part of application No. 10/501,394, filed as application No. PCT/CH03/00048 on Jan. 23, 2003, now abandoned.

(30) Foreign Application Priority Data

Mar. 21, 2011   (EP) .................................. 11158964

(51) Int. Cl.
*A61M 1/00* (2006.01)
*A61M 1/28* (2006.01)
*A61M 1/16* (2006.01)

(52) U.S. Cl.
CPC ............... *A61M 1/28* (2013.01); *A61M 1/1619* (2014.02); *A61M 1/287* (2013.01); *A61M 2202/0486* (2013.01)

(58) Field of Classification Search
CPC ..... A61M 1/1619; A61M 1/28; A61M 1/287; A61M 2202/0486; A61M 1/14; A61M 1/16; A61M 1/1601; A61M 1/1605; A61M 1/1609; A61M 1/1617

USPC .................................. 604/27, 29, 210, 321.6
See application file for complete search history.

(56) References Cited

U.S. PATENT DOCUMENTS

| | | | |
|---|---|---|---|
| 2,797,149 A | 6/1957 | Skeggs | |
| 4,177,677 A * | 12/1979 | Ruzicka et al. | ............ 73/863.71 |
| 4,244,787 A * | 1/1981 | Klein et al. | .................... 205/778 |
| 4,268,268 A | 5/1981 | Blum | |
| 4,452,682 A * | 6/1984 | Takata et al. | ............. 204/403.12 |
| 4,618,343 A | 10/1986 | Polaschegg | |

(Continued)

FOREIGN PATENT DOCUMENTS

| | | |
|---|---|---|
| DE | 30 19 670 A | 2/1981 |
| DE | 100 49 900 | 12/2001 |
| WO | WO 99/06082 | 2/1999 |

OTHER PUBLICATIONS

Third party Notice of Opposition by Fresenius Medical Care Deutschland GmbH dated May 30, 2011.
Twardowski Z.J., et al, *Peritoneal Dialysis Bulletin*, vol. 7, Sep. 1987; pp. 138-147; "Peritoneal Equilibration Test."
Schönweiß, Band 2, dritte, völlig neu bearbeitete und erweiterte Auflage, abakiss Verlags-GmbH, 2006; "Dialysefibel 3."
EPO Notice of Opposition dated Jun. 16, 2011.

(Continued)

*Primary Examiner* — Jason Flick
(74) *Attorney, Agent, or Firm* — Nixon & Vanderhye PC

(57) ABSTRACT

Device for determining the characteristics of peritoneal membrane comprising means for measuring glucose in the fluid drainage and a processing unit comprising means for determining the characteristics of the membrane as a function of that rate of glucose measured at different times. The invention also relates to a method for determining the characteristics of peritoneal membrane including the consideration of glucose measured at different moments in the liquid drainage.

20 Claims, 2 Drawing Sheets

(56) References Cited

U.S. PATENT DOCUMENTS

| | | | | |
|---|---|---|---|---|
| 4,784,157 A | * | 11/1988 | Halls et al. | 600/575 |
| 5,037,737 A | * | 8/1991 | Liffmann et al. | 435/11 |
| 5,066,283 A | * | 11/1991 | Skrabal | 604/152 |
| 5,670,057 A | * | 9/1997 | Chen et al. | 210/739 |
| 5,865,766 A | | 2/1999 | Bonsall et al. | |
| 5,902,253 A | * | 5/1999 | Pfeiffer et al. | 600/584 |
| 6,228,047 B1 | * | 5/2001 | Dadson | 604/29 |
| 6,595,948 B2 | | 7/2003 | Suzuki et al. | |
| 2002/0010553 A1 | | 1/2002 | Givens et al. | |
| 2002/0107474 A1 | | 8/2002 | Noack | |
| 2002/0162778 A1 | * | 11/2002 | Peabody et al. | 210/85 |

OTHER PUBLICATIONS

Final Office Action mailed Apr. 25, 2011 in U.S. Appl. No. 10/501,394.
Office Action mailed Oct. 14, 2010 in U.S. Appl. No. 10/501,394.
Office Action mailed Apr. 13, 2010 in U.S. Appl. No. 10/501,394.
Office Action mailed Jun. 11, 2009 in U.S. Appl. No. 10/501,394.
International Preliminary Examination Report dated Apr. 16, 2004.
Office Action mailed Jul. 25, 2008 in U.S. Appl. No. 10/501,394.
Office Action mailed Jan. 9, 2008 in U.S. Appl. No. 10/501,394.

* cited by examiner

DEVICE FOR DETERMINING THE CHARACTERISTICS OF PERITONEAL MEMBRANE

This application is a continuation-in-part of U.S. patent application Ser. No. 10/501,394 filed on Jul. 15, 2004, now abandoned which is the US national phase of international application PCT/CH03/00048 filed Jan. 23, 2003, which designated the U.S. and claims priority from PCT/CH02/00046, dated Jan. 28, 2002, and this continuation-in-part application also claims priority from European patent application EP 11158964.4, filed Mar. 21, 2011, the entire contents of all of which are hereby incorporated by reference.

The present invention relates to a peritoneal dialysis system which is programmed to deliver fluid to a peritoneal cavity of a patient and to drain the fluid from the cavity, said peritoneal dialysis system comprising a supplying line and supplying means for supplying dialysis fluid to the peritoneal cavity, a draining line and draining means for draining the fluid from the cavity.

Different tests have been proposed to evaluate the patient membrane characteristics in order to improve the exchanges of fluid during peritoneal dialysis according to each patient. For instance the PDC test according to Haraldsson and Rippe, based on the three pore model, is commonly used to achieve this objective. Other tests would also be of interest if they would be able to evaluate the specific outcome of a given peritoneal dialysis type of cycles for a given patient and be used to improve those cycles based on the peritoneal dialysis outcome.

However all present tests show some disadvantages and limitations. In particular they cannot be reliable enough due to the impossibility of carrying out measurements during certain periods such as dwell time. Those tests are also not able to directly evaluate the outcome of a given type of cycle but rather evaluate the membrane characteristics in order to calculate optimized cycles for the patient. With the PDC test for example, there must be a full exchange cycle before carrying the measurements on the drained volume. State of the art tests also not allow the automatic use of different liquids and/or different concentrations, nor the automatic sampling. Furthermore they are particularly cumbersome for the patient since they have to be manually done over a 24 h period of time, with typically 5 exchanges. Therefore, the use of those tests is today limited to certain patients and require specific conditions to be conducted.

One of the objects of the present invention is to avoid the previous listed problems.

It relates to a device for determining the characteristics of peritoneal membrane comprising means for direct measurement of glucose in a drain line and a processing unit comprising means for determining the characteristics of the membrane as a function of that rate of glucose measured at different moments.

A fundamental aspect of the invention is to characterize the membrane including the rate of glucose in the fluid drainage, without the need to conduct laboratory measurements, the results being obtained by direct reading at the moment samples taken using a glucose sensor available on the market that allows to transfer the results of these measures virtually instantaneously cycler. These steps are preferably made at predetermined time intervals, based on representative samples of the dialysate content in the peritoneum of the patient at the time of measurement. Knowing the nature of the initial dialysate injected into the peritoneum of the patient, reading the evolution over time of glucose can deduce the characteristics of the membrane of the patient using a specific algorithm. For a sufficient number of measurements at intervals of multiples of a cycle, said steps being repeated for several cycles with different time or different initial concentrations of the dialysate, we can deduce fairly accurately the characteristics of the peritoneal membrane without that is absolutely necessary to perform biochemical measures such as the measurement of urea, microglobulin, albumin, protein, sodium or creatinine for each cycle. Such additional measures may however be performed on a single sample of the total drain removed at the end of all cycles of exchange, in order not to complicate the measuring device and the cost of such an approach while improving the outcome Evaluation of the membrane. Added to this is the measurement of ultra-filtrate (total or per cycle), which can easily be obtained automatically by the cycler.

The device according to the invention preferably comprises means for taking at least one sample of peritoneal fluid during and at the end of at least one cycle of dialysis and a processing unit comprising means for determining the characteristics of the membrane as a function of that rate of glucose measured at different times.

Various embodiments of the invention are described in the claims.

Preferably, but not necessarily, the device according to the invention should carry out exchanges, preferably at night, traditional (or modified) with an APD cycler (as described in the patent of the plaintiff and EP1648537 U.S. Pat. No. 6,558, 343) and achieve measurement of glucose in the fluid drainage at different times. In this context, it is advantageous to use a wireless glucose sensor (eg sensor CGM Dexcom: "Seven") which transmits the information directly measured cycler. Such sensors are capable of measuring glucose levels continuously. According to one embodiment of the invention, simply perform a small tank (eg 3 ml) along the drain line so as to capture a certain volume of liquid drainage in which the needle is placed a glucose sensor. Preferably, this reservoir can be flushed automatically when the liquid drainage enters the tank, replacing the previous sample by a new sample at the desired time. Glucose measurements thus obtained can be directly sent to the cycler that can correlate the values at different points in the cycle of patient care. The data can then be transferred to a computer that can make a calculation of the characteristics of the membrane.

It is also possible to use a glucose sensor fast enough to make a continuous measurement in the liquid drainage and thus be able to discriminate the liquid to be analyzed (representative of the test portion) based on measured values, the value appearing after a certain desired volume has been drained (dead space) and can therefore be recognized that this value is different from that measured before the drainage until the value stabilizes. Using such a method may include automated measurement to drain until a stable value that is representative of the concentration in the peritoneum.

Preferably, performing a measurement on a sample during the phase of stasis and a sample during the final drainage, the amount of glucose being a priori known at the time of filling. We can also make a measurement of glucose immediately after filling the peritoneal cavity with fresh dialysate fluid, to derive the dilution of the liquid filling charges with the remaining liquid before the cycle has not been drained or an Ultra Filtration. Such a measure allows to know the real rate of glucose present at the initial time of the cycle and to estimate the total actual amount of fluid in the peritoneum during this cycle.

In order to receive maximum information on the rate of glucose in the peritoneum of the patient during the time that is peritoneal dialysis and thus better able to evaluate the characteristics of the membrane (a larger number of points measures to make the assessment of the characteristics of the membrane more reliable), is preferably made drainage at multiple intervals are measured individually as described above. For example, we can make some drainages ml every 10 minutes during the time of a cycle of dialysis and usually lasts 2 hours, 11 samples over that corresponding to the final drain. Of course, should be considered for each sample of the dead volume of tubing between the catheter tip in the peritoneum of the patient and the measuring chamber, which will require adding a minimum volume of said chamber and a possible additional volume to avoid sampling a liquid that is not representative of the average concentration in the peritoneum (possibly due to a retention effect in a pocket, as the pouch of Douglas). In order not to change dialysis after collection, specimens should be less than 200 ml, ideally 30 to 100 ml if samples must be repeated. It should also ensure that the liquid remains in said measuring chamber a minimum time to allow the sensor to perform a minimum number of measures to ensure the required accuracy (in the case of sensor Dexcom, the minimum time is 5 minutes today but could be lower in new generations of sensors).

It may also stir the fluid in the peritoneum in order to improve mixing, for example using an electric mattress that shakes the patient before each sampling.

To receive the most accurate settings, relative to the model described by three pores Börje Haraldsson and Bengt Ripper, there should be preferably exchanges with dialysis products with concentrations of glucose cycles vary, and preferably with cycles of varying durations (eg several cycles of 2 hours and a long cycle of 4 hours). Such exchanges can easily be realized in one night by an APD cycler and direct debits to be made by short drainage and low volume did not affect peritoneal dialysis itself during each cycle.

To obtain more complete information to estimate all the functional parameters of the patient's peritoneal membrane as appropriately as possible, without representing a major constraint or a substantial additional cost, it is desirable to have values of Ultra Filtration, if possible for each cycle (the measurement being performed automatically by the cycler at the end of each cycleset at minimu, the last cycle for the calculation of the total), the average rate of various substances (urea, creatinine, sodium, albumin, or even certain proteins or solutes) that will be analyzed in the laboratory on the basis of a sample taken by the patient in the total dialysate. It may also be useful to have the measure of the rate of sodium (eg using a conductance measurement in the measuring tank), or multiple intervals, either at the end of each cycle. It may also be useful to measure the pH in the same conditions. All this information is then collected and taken into consideration in establishing meaningful values of the membrane, preferably the three pore model.

Based on these data, knowing the characteristics of the membrane to intervals course (a few months instead of one year or more for testing complex as the PDC test) it is possible to better predict the result of a peritoneal dialysis on a patient and better tailor treatment. It is also possible because of the simplicity of the test method described according to the invention, to repeat these measurements at regular intervals to establish a pattern of development to better monitor the patient and adapt faster processing. The cost of such a test is very limited (at least the cost of a glucose sensor, which can optionally be used for multiple tests) or even better a blood test and a biochemical test on a single specimen of the total drain it is easy to repeat at regular intervals without it represents a particular constraint for the patient (such a test can even be done on the basis of customary exchange of patient including, when possible, a long cycle).

The device and method of the invention can be advantageously used in combination with a sampling device as described in Patent Application EP 1469896 to conduct laboratory measurements of individual samples so withdrawn.

When used, the automatic sampling system is connected on the draining line either between the patient peritoneum and the draining means or between the draining means and a waste collector.

Connecting the automatic sampling system according to the invention on the draining line allows to carry out a test at any time by drawing liquid directly from the peritoneum. It also allows to take samples of fluid at different points of time and having different sample volumes during the same cycle. All these possibilities improve considerably the evaluation of the peritoneal membrane characteristics and/or the peritoneal dialysis outcome for a given patient.

In particular, the possibility to increase the number of sampling steps and automatically vary the dialysate volume and concentration over a certain period of time allows to increase the number of information collected over a limited period of time. As a result, a full and more detailed patient peritoneal membrane evaluation can be made over a shorter period of time, allowing such evaluation to be conducted automatically preferably overnight. In certain circumstances, it may be useful to add one or several more manual samplings over the day, although the more detailed information would have been collected over the night by use of the automatic sampling system according to the present invention.

Preferably the automatic peritoneal dialysis sampling system is provided with means for defining the specific time intervals for sampling volumic fractions in relation with the peritoneal dialysis program sequences.

The evaluation of the peritoneal membrane characteristics may be improved by providing the automatic peritoneal dialysis sampling system with means, e.g. a system of valves and separate fluidic paths, in order to sample different peritoneal dialysis fractions and collect them in separate containers for a later detailed analysis of their specific content.

The automatic peritoneal dialysis sampling system may be connected between the patient peritoneum and the draining means, requiring sampling means to sample liquid from the peritoneum at different points of time. The sampling means may, for example, be of a peristaltic type allowing a precise volumic sampling. Alternatively, the sampling means may result from vacuum originating from the sampling containers which may be controlled by a series of valves, or by gravity. In another embodiment of the present invention the automatic peritoneal dialysis sampling system may be connected after the draining means, such draining means being used, in such case, for both draining the dialysis fluid after each cycle as well as collecting the sampling fractions. In the event of dwell time sampling, the draining means would be activated to sample the volumic fraction required during dwell time, while in the drain phase of each cycle only a fraction of the drainage volume would be collected by use, for example, of a valve system.

The connection of the automatic peritoneal dialysis sampling system to the draining line may also be made by an electromechanical valve which is actuated in relation with a specific functioning of the draining means.

When the connection of the automatic peritoneal dialysis sampling system to the draining line is situated between the patient peritoneum and the draining means, the automatic sampling can be made during the dwell time of the peritoneal dialysis cycle and/or during the drain cycle without interfering with the peritoneal dialysis system. When the connection of the automatic peritoneal dialysis sampling system is situated after the draining means, the automatic sampling can only occur during the drain phase of each cycle or, alternatively, can also occur during the dwell time provided the draining means are activated during such dwell time for that purpose. In the first case, the automatic peritoneal sampling system requires sampling means, while in the latest case the draining means of the peritoneal dialysis system are also used for sampling purposes.

The sampling means, if required, preferably include pumping means such as a peristaltic pump. They may also be of a gravity type, or vacuum type, if in connection with a series of valves.

In a preferred embodiment the automatic sampling system comprises a series of sampling containers, pumping means and a series of valves in order to direct a certain quantity of each fluid sample to a given sampling container.

The sampling containers may consist of soft pouches.

The automatic sampling system may be composed of a series of valves which are controlled by an electronic system in order to direct a certain quantity of each fluid sample to a specific sampling container. The valves may be of electromagnetic type.

Preferably the automatic sampling system comprises means for eliminating a volume of liquid between two samplings at least equivalent to the dead volume contained between the patient and the sampling level. This can be done by providing the system with a purging line. With such a configuration, after a first sampling, the draining line is connected to the purging line in order to purge the above cited dead volume in order to prevent mixing of two different samples. A second sampling occurs then when the draining line is connected to another sampling container. Purging can be obtained either by use of the sampling means or, in the configuration with draining means from the automatic peritoneal dialysis system, by use of such draining means.

Advantageously, both systems: the peritoneal dialysis system which comprises an automatic peritoneal dialysis exchange system, and the automatic peritoneal dialysis sampling system are connected to the patient peritoneum and comprise means for exchanging information together in order for the automatic peritoneal dialysis sampling system to determine the appropriate timing for each sampling on the basis of the dialysis exchange cycles of the automatic peritoneal dialysis exchange system.

In a further embodiment, the automatic sampling system under the present invention can also be used to not only determine the membrane characteristics but also evaluate one or several peritoneal dialysis exchange cycles in order to determine the best appropriate exchange cycle or series of cycles for the patient.

In a preferred embodiment both automatic peritoneal dialysis sampling system and automatic peritoneal dialysis exchange system are similar systems which are synchronized and which are working with different software and fluidic connections. For instance, they both may comprise peristaltic pumps.

In another preferred embodiment of the present invention, the automatic peritoneal dialysis sampling system only consist of a series of electro-valves and containers, which electro-valves are controlled by the automatic peritoneal dialysis system. In such preferred embodiment, the sampling is directed from the peritoneum to the containers by use of the drawing means of the automatic peritoneal dialysis system which contains a specific order of sequence for the opening and closing of specific valves in connection with the peritoneal dialysis cycles.

The peritoneal dialysis system may comprise a memory key which contains all the necessary data to program the functioning of said automatic peritoneal dialysis sampling system according to the peritoneal dialysis cycles and to store the sampling information.

The automatic peritoneal dialysis sampling system may comprise means for sequentially collecting sample volumes in a tubing, each sample being separated from the previous one by an air bubble inserted by the automatic peritoneal sampling system in-between each sample.

In order to store the samples in optimal conditions until analysis the sampling containers may preferably be enclosed inside a cooling box which comprises cooling means.

Advantageously the automatic peritoneal dialysis sampling system comprises analyzing means for directly analyzing of at least one characteristic of the sample in-line, such as by spectroscopy, fluorometry or by use of chemical or electrochemical means.

The automatic sampling system may be adapted to measure different constituents/parameters in addition to glucose, such as urea, creatinine, sodium, chloride, albumine, proteins, osmolarity or ph.

For instance the result of the in-line analysis is used to optimize the next peritoneal dialysis exchange cycle or sampling intervals in order to improve the membrane characteristics evaluation or directly evaluate the impact of specific changes on the peritoneal dialysis outcome for the patient.

Some embodiments of the invention will be discussed hereafter in a more detailed way.

Figure 1:
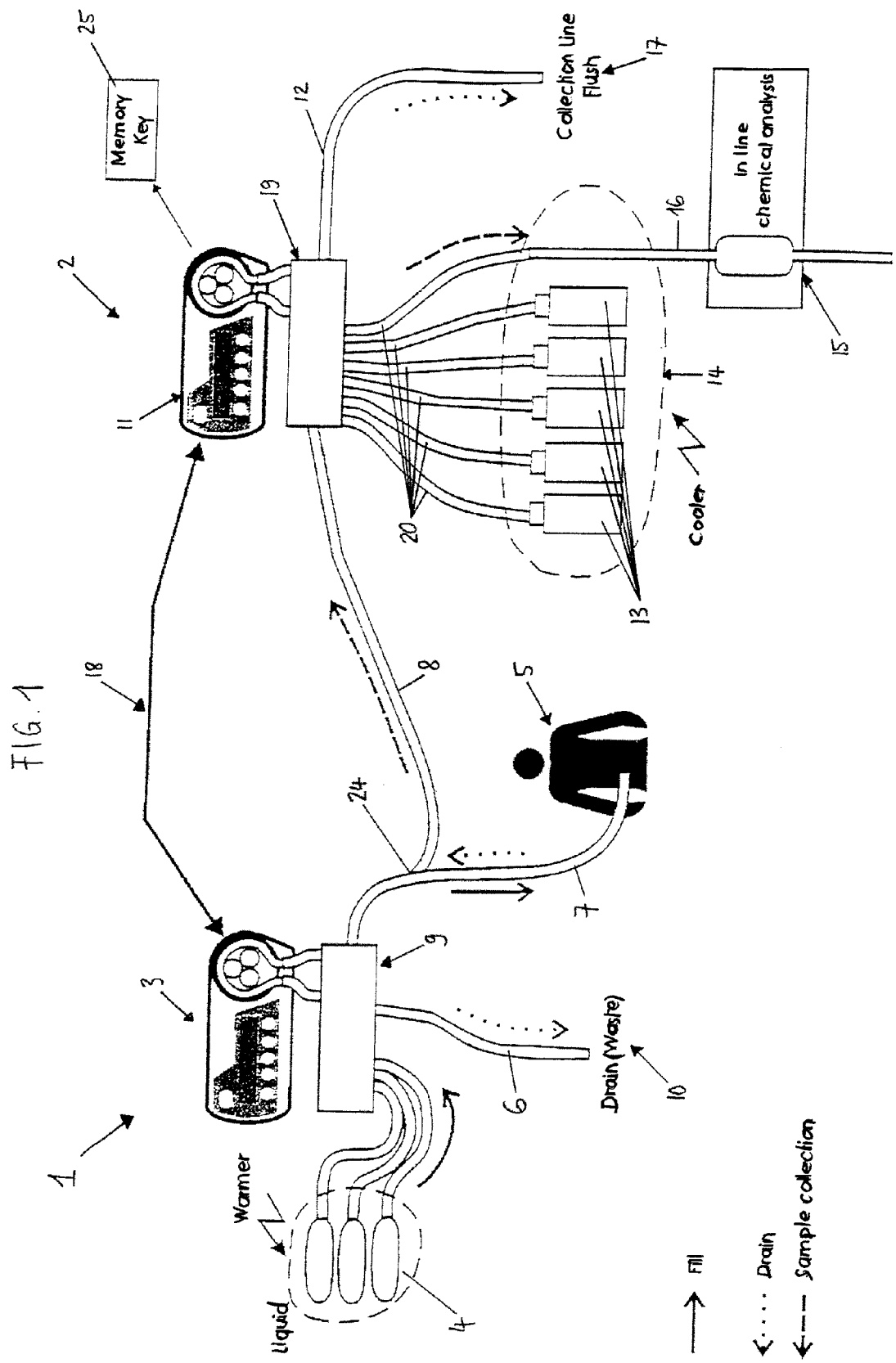
FIG. 1 illustrates a first embodiment of the system according to the invention where the automatic sampling system is connected on the draining line between the patient peritoneum and the draining means.

The peritoneal dialysis system according to FIG. 1 consists of a first system 1 comprising a first peristaltic pump 3, dialysis fluid containers 4, a line 6,7 consisting of a supplying/draining line 7 which is arranged between a patient 5 and the first peristaltic pump 3 and a draining line 6 which is arranged between the first peristaltic pump 3 and a first waste collector 10, the dialysis fluid containers 4 and the draining line 6 may be alternatively connected to the supplying/draining line 7 by a valve 9 e.g. of electromechanical type.

The supplying/draining line 7 is provided with a Y-site 24 in order to connect a sampling line 8. The peritoneal dialysis system according to FIG. 1 also includes an automatic sampling system 2 made of a second peristaltic pump 11, a collection line 12, sampling containers 13 linked to the sampling line 8 via conduits 20 and a analyzing line 16 comprising an analyzing unit 15. The sampling line 8, the conduits 20, the analyzing line 16 and the collection line 12 are all alternatively connected to the second peristaltic pump 11 by an appropriate valve 19. The sampling containers 13 are arranged within a cooling container 14. Both first system 1 and the automatic sampling system 2 may change information via a communication line 18 (by cable or by wireless communication). The automatic sampling system 2 is provided with a memory key 25 which contains all the necessary data to program the functioning of said automatic peritoneal dialysis sampling system and to store the sampling information.

The automatic sampling system 2 can be programmed to take volumic fractions of liquid at predetermined times, for instance during the dwell time. Those volumic fractions may differ from each other. The volumic fractions may also be taken during the drain cycle. The collection line 12 allows to purge a dead volume between samplings.

Figure 2:
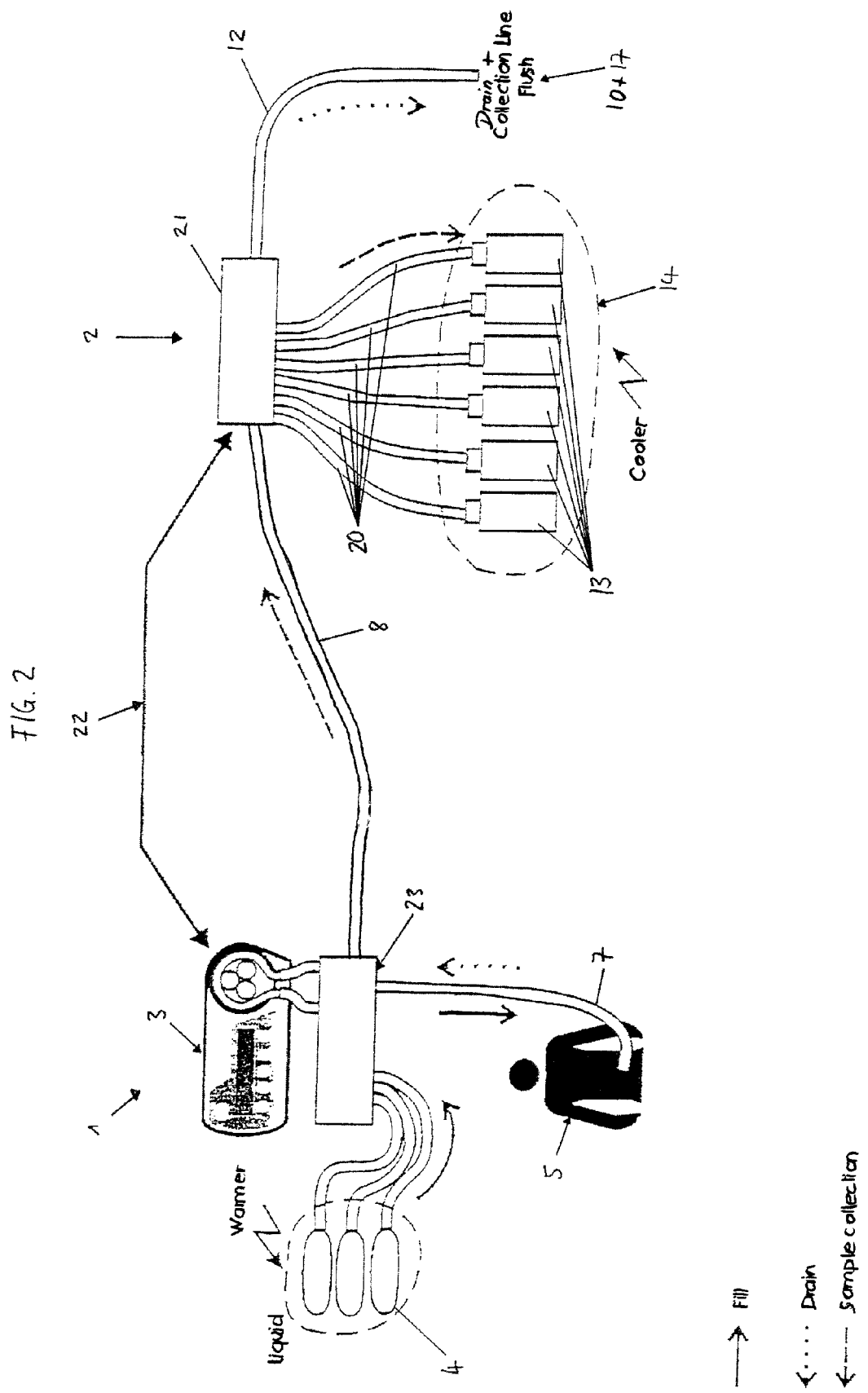
FIG. 2 illustrates another embodiment of the system according to the invention where the automatic sampling system is connected on the draining line between the draining means and a waste collector.

FIG. 2 shows another configuration, very similar to the configuration of FIG. 1, but which uses only one peristaltic pump 3 for supplying dialysis liquid to the patient, draining dialysis fluid from the patient and supplying volumic fractions to the automatic sampling system 2. In this configuration, the sampling line 8 is connected on the draining line 6. In said configuration, sampling are controlled by the peristaltic pump which may be activated for sampling purposes at any time, including during the dwell time.

Obviously the invention is not limited to the examples cited above, different cycles, coveralls, levies and/or measures that can be added to improve the outcome of the evaluation of membrane characteristics of the patient. The invention also encompasses any automatic sampling system 2 which can take volumic fractions of liquid during a dwell cycle or a drain cycle.

The invention claimed is:

1. A device for determining characteristics of a peritoneal membrane in order to improve exchanges of fluid during peritoneal dialysis, said device comprising
    an automatic peritoneal dialysis sampling system that automatically samples, at specific time intervals, volumic fractions of a dialysate contained in a peritoneum of a patient in order to evaluate the peritoneal membrane characteristics,
    wherein the sampling system comprises an analyzing unit for directly analyzing at least one characteristic of the sample in a drain line, by spectroscopy or fluorometry or by use of a chemical or electro-chemical analysis,
    wherein the at least one characteristic is glucose, and
    whereby the device's automatic sampling of the volumic fractions of the dialysate contain in the peritoneum of the patient at specific time intervals evaluates the glucose at the specific time intervals.

2. The device according to claim 1 comprising a measuring tank adapted to be disposed along the drain line, said measuring tank having at least one glucose sensor.

3. The device according to claim 1, wherein said device employs at least two cycles of dialysis performed with different initial concentrations of glucose and/or different durations.

4. The device according to claim 1, comprising a glucose sensor adapted to continuously measure glucose levels in an area of the drain line.

5. The device according to claim 1, comprising means for measuring levels of sodium in the drain line, said device also taking into account the levels of sodium in determining the characteristics of the peritoneal membrane.

6. The device according to claim 1, comprising means for measuring biochemical parameters, whereby the biochemical parameters are also taken into account in determining the characteristics of the peritoneal membrane.

7. The device according to claim 1, wherein a means for direct measurement of glucose in the drain line is a wireless sensor.

8. The device according to claim 1, comprising means for taking at least one sample of peritoneal fluid during and at an end of at least one round of dialysis.

9. A method of determining characteristics of peritoneal membrane in order to improve exchanges of fluid during peritoneal dialysis, said method using the device according to claim 1 and including measuring glucose at different moments in a drain line.

10. The method of claim 9 wherein at least one sample is taken during a stasis and a sample taken during a drainage phase.

11. The method of claim 9, wherein multiple samples are taken at regular intervals (or variables) for a cycle.

12. The method according to claim 9, wherein a sample is taken immediately or shortly after startup (filling the peritoneum) of a cycle.

13. The method according to claim 9, used as part of an automated cycle including at least one night-long cycle longer than two hours.

14. The method according to claim 9, used as part of an automated nightly cycle including at least two cycles with different concentrations of glucose.

15. The method according to claim 9, used as part of an automated cycle including at least one cycle with a solution of sodium concentration reduced.

16. The method according to claim 9, including the use of a three-pore model.

17. The method according to claim 9, comprising a sampling of fluid drainage and measurement of glucose levels in the sampling.

18. The method of claim 17, wherein one considers a dead volume of a tube during the sampling.

19. The method according to claim 17, wherein each sampling is less than 200 ml.

20. The device according to claim 6, wherein the biochemical parameters are creatine, urea, microglobulin, protein, albumin, or pH.

* * * * *